United States Patent [19]

Aburaki et al.

[11] 4,406,899

[45] Sep. 27, 1983

[54] CEPHALOSPORINS

[75] Inventors: Shimpei Aburaki, Tokyo; Hajime Kamachi, Urayasu; Yukio Narita; Jun Okumura, both of Yokohama; Takayuki Naito, Kawasaki, all of Japan

[73] Assignee: Bristol-Myers Company, New York, N.Y.

[21] Appl. No.: 354,851

[22] Filed: Mar. 4, 1982

[51] Int. Cl.³ .................. A61K 31/545; C07D 501/46
[52] U.S. Cl. ....................................... 424/246; 544/22
[58] Field of Search .......................... 544/22; 424/246

[56] References Cited

U.S. PATENT DOCUMENTS 4,168,309  9/1979  Ayres ..................................... 544/22
4,278,671  7/1981  Ochiai et al. .......................... 544/22
4,278,793  7/1981  Durckheimer et al. .............. 544/22

FOREIGN PATENT DOCUMENTS 2805655  8/1978  Fed. Rep. of Germany .
1399086  6/1975  United Kingdom .

Primary Examiner—Paul M. Coughlan, Jr.
Attorney, Agent, or Firm—Richard R. Lloyd

[57] ABSTRACT

Compounds of the formula

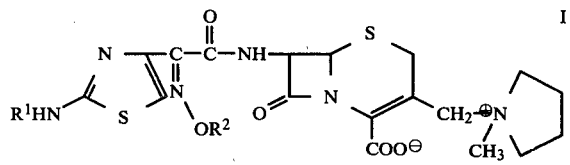

wherein $R^1$ is hydrogen or a conventional amino-protecting group, and $R^2$ is a straight or branched chain alkyl group containing from 1 to 4 carbon atoms, allyl, 2-butenyl or 3-butenyl, and nontoxic pharmaceutically acceptable salts and solvates thereof, as well as processes for their preparation, are disclosed. The compounds in which $R^1$ is hydrogen are potent antibacterial agents.

11 Claims, No Drawings

CEPHALOSPORINS

SUMMARY OF THE INVENTION

This invention relates to novel cephalosporin derivatives of the formula

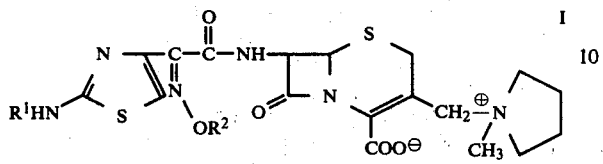

wherein $R^1$ is hydrogen or a conventional amino-protecting group, and $R^2$ is a straight or branched alkyl group containing from 1 to 4 carbon atoms, allyl, 2-butenyl or 3-butenyl, and nontoxic pharmaceutically acceptable acid addition salts or solvates thereof. Processes for their preparation are also described.

DESCRIPTION OF THE PRIOR ART

U.K. Pat. No. 1,399,086 contains a generic disclosure encompassing a vast number of cephalosporins of the formula

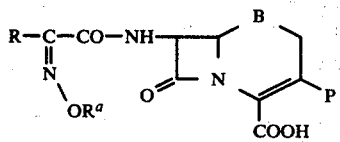

wherein R is hydrogen or an organic group, $R^a$ is an etherifying monovalent organic group linked to the oxygen through a carbon atom, B is $>S$ or $>S\rightarrow O$, and P is an organic group. However, the 2-aminothiazol-4-yl group is not identified as an R substituent and there is no suggestion that P may be N-methylpyrrolidinium-methyl (or any other fully saturated nitrogen-containing ring which is attached to the 3-methyl moiety via its nitrogen atom and which contains an additional substituent on its nitrogen atom). U.S. Pat. No. 3,971,778 and its divisionals U.S. Pat. Nos. 4,024,133, 4,024,137, 4,064,346, 4,033,950, 4,079,178, 4,091,209, 4,092,477 and 4,093,803 have similar disclosures.

U.S. Pat. No. 4,278,793 contains a generic disclosure encompassing a vast number of cephalosporin derivatives of the formula

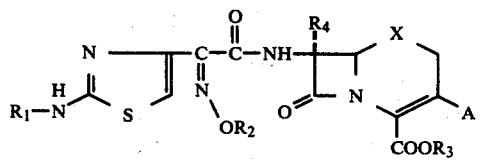

in which the variables $R_1$, $R_2$, $R_3$, $R_4$, X and A include generic definitions of the corresponding substituents of the compounds of Formula I claimed herein. However, in the 20 columns of definitions of the various substituent groups, the 78 page long table of structural formulae and the 225 examples, there is no disclosure that A may be N-methylpyrrolidiniummethyl (or any other fully saturated nitrogen-containing heterocyclic ring which is attached to the 3-methyl moiety via its nitrogen atom and which contains an additional substituent on its nitrogen atom. U.K. Pat. No. 1,604,971 is concordant thereto and has a substantially identical disclosure. Published United Kingdom patent application No. 2,028,305 A, although apparently not formally related, contains the same broad generic disclosure but exemplifies A only as hydrogen.

West German OLS No. 2,805,655 discloses 7-[2-(2-aminothiazol-4-yl)-2-(syn)methoxyiminoacetamido]-cephalosporanic acid derivatives of the formula

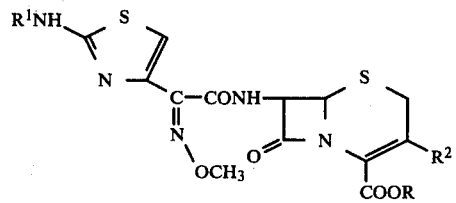

in which $R^1NH$ is an optionally protected amino group, $R^2$ is halogen or an optionally substituted hydroxyl, thiol or amino group, and COOR is an optionally esterified carboxyl group. It is also disclosed that, when $R^2$ is an amino group, it may be disubstituted and the substituents, taken together with the N atom, may form inter alia a pyrrolidino group. However, there is no disclosure of an N-methylpyrrolidinium group (or of any other quaternary ammonium group) and substituent $R^2$ cannot be connected to the 3-position via a methylene group.

U.S. Pat. No. 4,278,671 discloses 7-[2-(2-aminothiazol-4-yl)-2-(syn)-methoxyiminoacetamido]cephalosporin derivatives of the formula

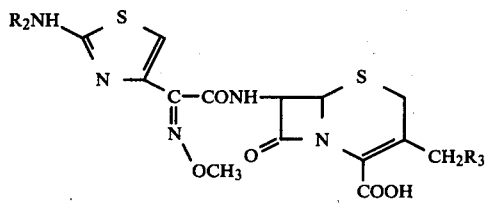

in which $R_2NH$ is an optionally protected amino group and $R_3$ is hydrogen or "the residue of a nucleophilic compound". The term "the residue of a nucleophilic compound" is broadly defined and it is then stated that $R^3$ "may alternatively be a quaternary ammonium group". Pyridinium, variously substituted pyridinium, quinolinium, picolinium and lutidinium are disclosed as quaternary ammonium groups. There is no suggestion that the quaternary ammonium group may consist of a fully saturated nitrogen-containing heterocyclic ring system which is bound via its nitrogen atom and which contains an additional substituent on its nitrogen atom. U.K. Pat. No. 1,581,854 is concordant thereto and has a substantially identical disclosure. Other patents to the same patentee, which are not formally related but which have similar disclosures, include U.S. Pat. No. 4,098,888 and its divisionals U.S. Pat. Nos. 4,203,899, 4,205,180 and 4,298,606, and U.K. Pat. No. 1,536,281.

U.S. Pat. No. 4,168,309 discloses cephalosporin derivatives of the formula

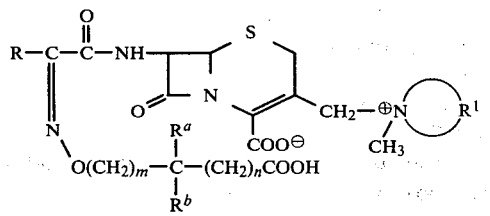

wherein R is phenyl, thienyl or furyl, and the compound having the formula

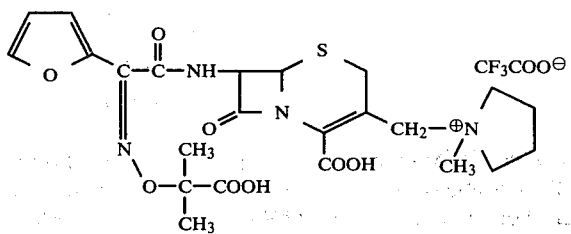

is exemplified in Example 5 thereof. U.K. Pat. No. 1,591,439 is concordant thereto and has a substantially identical disclosure. There is no suggestion in this patent that the R substituent may be the 2-aminothiazol-4-yl moiety or that the imino substituent not contain a carboxyl group.

COMPLETE DISCLOSURE

This invention relates to cephalosporin derivatives of the formula

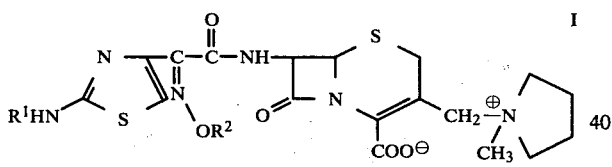

wherein $R^1$ is hydrogen or a conventional amino-protecting group, and $R^2$ is a straight or branched chain alkyl group containing from 1 to 4 carbon atoms, allyl, 2-butenyl or 3-butenyl, and nontoxic pharmaceutically acceptable salts thereof. Also included within the scope of this invention are the solvates (including hydrates) of the compounds of Formula I, as well as the tautomeric forms of the compounds of Formula I, e.g. the 2-imino-thiazolin-4-yl form of the 2-aminothiazol-4-yl moiety.

As shown in the structural formula, the compounds of Formula I have the "syn" or "Z" configuration with respect to the alkoxyimino (or alkenyloxyimino) group. Because the compounds are geometric isomers, some of the "anti" isomer may also be present. This invention comprises compounds of Formula I containing at least 90% of the "syn" isomer. Preferably the compounds of Formula I are "syn" isomers which are essentially free of the corresponding "anti" isomers.

The nontoxic pharmaceutically acceptable acid addition salts of the compounds of Formula I include the salts with hydrochloric, hydrobromic, formic, nitric, sulfuric, methanesulfonic, phosphoric, acetic and trifluoroacetic acids, and other acids which have been used in the penicillin and cephalosporin art.

The compounds of Formula I in which $R^1$ is hydrogen exhibit high antibacterial activity against various Gram positive and Gram negative bacteria, and are useful in the treatment of bacterial infections in animals, including man. The compounds of Formula I may be formulated for parenteral use in a conventional manner utilizing known pharmaceutical carriers and excipients, and may be presented in unit dosage form or in multi-dosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. The compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage for adult human treatment will preferably be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

The preferred compounds of Formula I are those in which $R^1$ is hydrogen and $R^2$ is methyl or ethyl. In the most preferred compound, $R^2$ is methyl. In the primary evaluation of the compounds of this invention, the Minimum Inhibitory Concentrations (MIC's) of the compounds and two reference compounds (cefotaxime and ceftazidime) were determined by the two-fold serial agar dilution method in Mueller-Hinton agar against 32 strains of test organisms in six groups. The geometric means of the MIC's determined in this test are shown in Table 1.

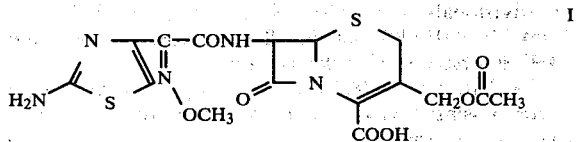

(Cefotaxime; Comparison Compound)

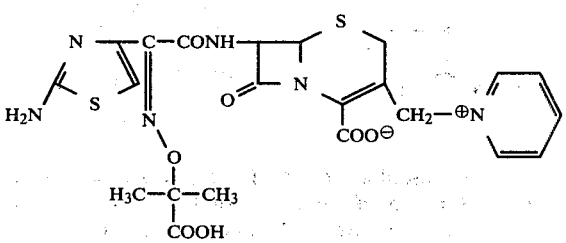

(Ceftazidime; Comparison Compound)

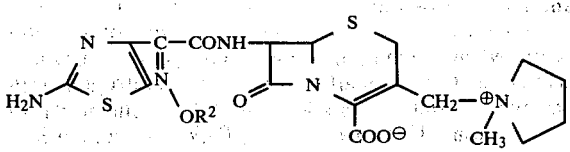

(Test Compounds)

It may be seen that all of the test compounds were more active then cefotaxime against the (G−)-II and (G−)-III groups of test organisms, with the most preferred Compound Ia being markedly more active. All of the test compounds were more active than ceftazidime against the (G+)-Ia and (G+)-Ib groups of test organisms, with the most preferred Compound Ia being markedly more active than ceftazidime against all groups of test organisms except (G−)-III, which was somewhat more susceptible to ceftazidime.

The absorption of the most preferred Compound Ia and of reference compounds (cefotaxime and ceftazidime) were determined in mice following a single intramuscular injection of the test compound (dissolved in 0.1 M phosphate buffer; pH 7) at a dosage of 20 mg/kg. Blood samples were collected from the orbital sinuses into heparinized capillary tubes and assayed in Mueller-Hinton medium using *Morganella morganii* A9695 as the test organism. The blood levels at various time intervals, the half-life values ($t_{\frac{1}{2}}$) and the areas under the curve (AUC) are shown in Table 2.

Tests to identify organisms resistant to the preferred compound of Formula Ia, cefotaxime and ceftazidime were also conducted. The MIC's of these three compounds against 240 strains of Enterobacteriaceae were determined in Mueller-Hinton medium, and an MIC of equal to or greater than 8 for at least one of the test compounds was arbitrarily taken as indicating a resistant organism. Of the 240 strains, 27 were found to be resistant to at least one of the test compounds. The results, showing 3 organisms resistant to Compound Ia, 15 organisms resistant to ceftazidime and 18 organisms resistant to cefotaxime, are given in Table 3.

TABLE 1

| | Geometric Mean of MIC (mcg/mL) | | | | | |
|---|---|---|---|---|---|---|
| Compound | (G+)-Ia (5 strains) | (G+)-Ib (5) | (G−)-Ia (5) | (G−)-Ib (6) | (G−)-II (5) | (G−)-III (6) |
| Ia; $R^2$ = methyl | 1.2 | 3.1 | 0.025 | 0.13 | 0.33 | 2.8 |
| Ib; $R^2$ = ethyl | 1.4 | 3.1 | 0.087 | 0.32 | 1.0 | 5.6 |
| Ic; $R^2$ = isopropyl | 1.4 | 3.6 | 0.35 | 1.3 | 3.2 | 11 |
| Id; $R^2$ = allyl | 1.8 | 3.6 | 0.53 | 1.1 | 2.4 | 13 |
| Cefotaxime[a] | 1.0 | 2.2 | 0.015 | 0.35 | 4.1 | 22 |
| Ceftazidime[a] | 5.1 | 12 | 0.070 | 1.7 | 2.6 | 1.8 |

(G+)-Ia: Penicillin-sensitive *S. aureus* (5 strains)
(G+)-Ib: Penicillin-resistant *S. aureus* (5 strains)
(G−)-Ia: Cephalothin-sensitive *E. coli* (2 strains), *Kl. pneumoniae* (1 strain) and *Pr. mirabilis* (2 strains)
(G−)-Ib: Cephalothin-resistant *E. coli* (3 strains) and *Kl. pneumoniae* (3 strains)
(G−)-II: *Pr. morganii* (1 strain), *Ent. cloacae* (2 strains) and *Ser. marcescens* (2 strains)
(G−)-III: *Ps. aeruginosa* (6 strains)
[a] Mean of five experiments

TABLE 2

Blood Levels After Intramuscular Administration to Mice (20 mg/kg)

| | Blood Levels (mcg/mL) Minutes After Administration | | | | | | $t_{\frac{1}{2}}$ (minutes) | AUC (mcg · hour/ml) |
|---|---|---|---|---|---|---|---|---|
| Compound | 10 | 20 | 30 | 45 | 60 | 90 | | |
| Ia; $R^2$ = methyl[a] | 20.7 | 19.6 | 13.6 | 8.8 | 4 | ~0.9 | 17 | 13.5 |
| Cefotaxime[b] | 27.8 | 19.3 | 13 | 9.1 | 4.6 | 1.2 | 15 | 14.9 |
| Ceftazidime[c] | 21.5 | 18.4 | 14.9 | 8.7 | 4.4 | ~0.8 | 17 | 13.8 |

[a] average of 2 tests
[b] 1 test
[c] average of 3 tests

TABLE 3

Resistance (MIC = ≧8 μg/ml) to One or More Test Compounds Among 240 Strains of Enterobacteriaceae in Mueller-Hinton Medium

| Organism | No. of Strains | Geometric Mean MIC (μg/ml) | | |
|---|---|---|---|---|
| | | Ia | Ceftazidime | Cefotaxime |
| *Escherichia coli* | 1 | 0.25 | 32 | 8 |
| *Escherichia coli* | 1 | 4 | 0.5 | 8 |
| *Klebsiella pneumoniae* | 1 | 2 | 16 | 0.13 |
| *Enterobacter aerogenes* | 3 | 0.25 | 32 | 13 |
| *Enterobacter aerogenes* | 1 | 4 | 8 | 32 |
| *Enterobacter cloacae* | 1 | 0.13 | 4 | 8 |
| *Enterobacter cloacae* | 3 | 0.5 | 40 | 50 |
| *Enterobacter cloacae* | 3 | 1.6 | >63 | >63 |
| *Enterobacter cloacae* | 1 | >32 | >63 | >63 |
| *Citrobacter freundii* | 2 | 0.35 | 45 | 32 |
| *Citrobacter species* | 1 | 0.03 | >63 | 32 |
| *Proteus vulgaris* | 1 | 0.06 | 8 | 8 |
| *Morganella morganii* | 1 | 0.06 | 32 | 32 |
| *Serratia marcescens* | 1 | 1 | 1 | 16 |
| *Serratia marcescens* | 1 | 2 | 8 | 16 |
| *Serratia marcescens* | 2 | 2.8 | 2 | 11 |
| *Serratia marcescens* | 1 | 4 | 8 | 63 |
| *Serratia marcescens* | 1 | 8 | 16 | 8 |
| *Serratia marcescens* | 1 | 32 | >63 | >63 |
| Total Number of Resistant Strains | 27 | 3 | 15 | 18 |

In another aspect, this invention relates to processes for the preparation of the compounds of Formula I. There are two basic procedures for converting a readily available starting cephalosporin to another cephalosporin having different substituents on the 7- and 3-positions. One may first remove the 7-substituent and replace it with the desired 7-substituent, and then insert the desired 3-substituent. Alternatively, one may first insert the desired 3-substituent and subsequently exchange the 7-substituent. The compounds of Formula I may be prepared by either procedure and both are included within the scope of this invention, but it is preferred to insert the desired 7-substituent first and then insert the desired 3-substituent. The preferred procedure is shown below in Reaction Scheme 1 while the alternative procedure is shown in Reaction Scheme 2. The abbreviation "Tr" represents the trityl (triphenylmethyl) group, which is a preferred amino-protecting group. The abbreviation "Ph" represents the phenyl group. Thus, the —CH(Ph)₂ moiety is the benzhydryl group, which is a preferred carboxyl-protecting group.

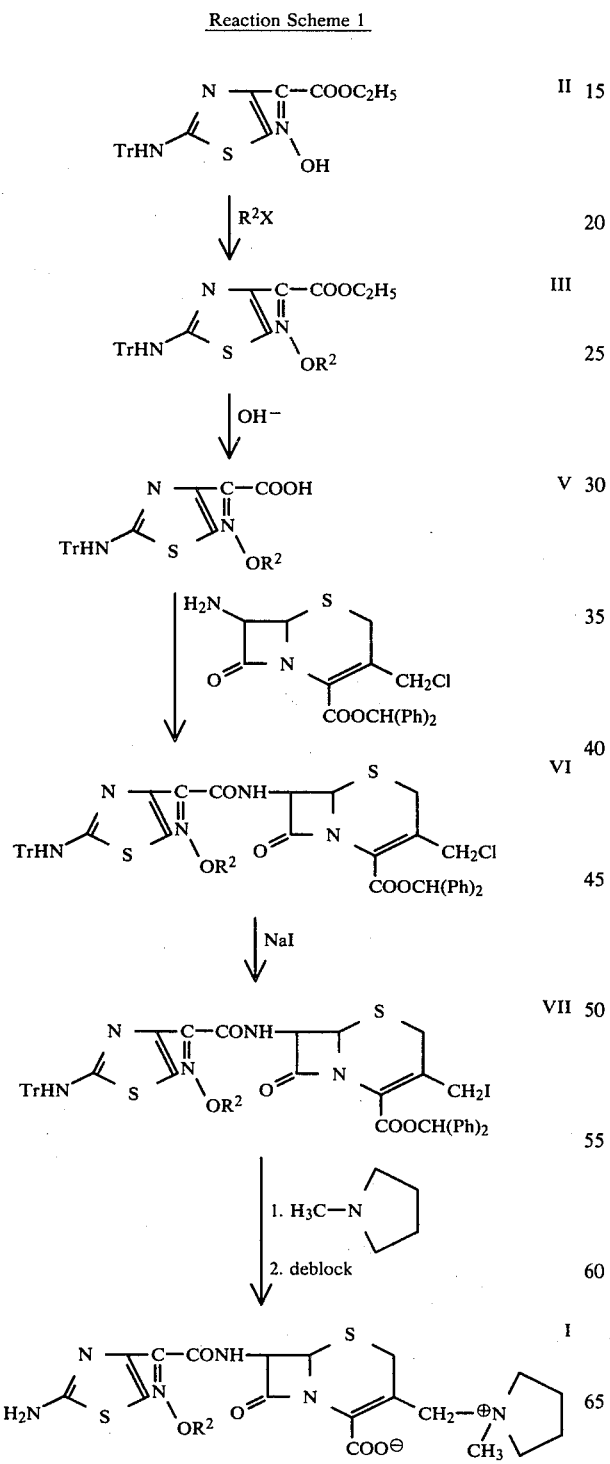

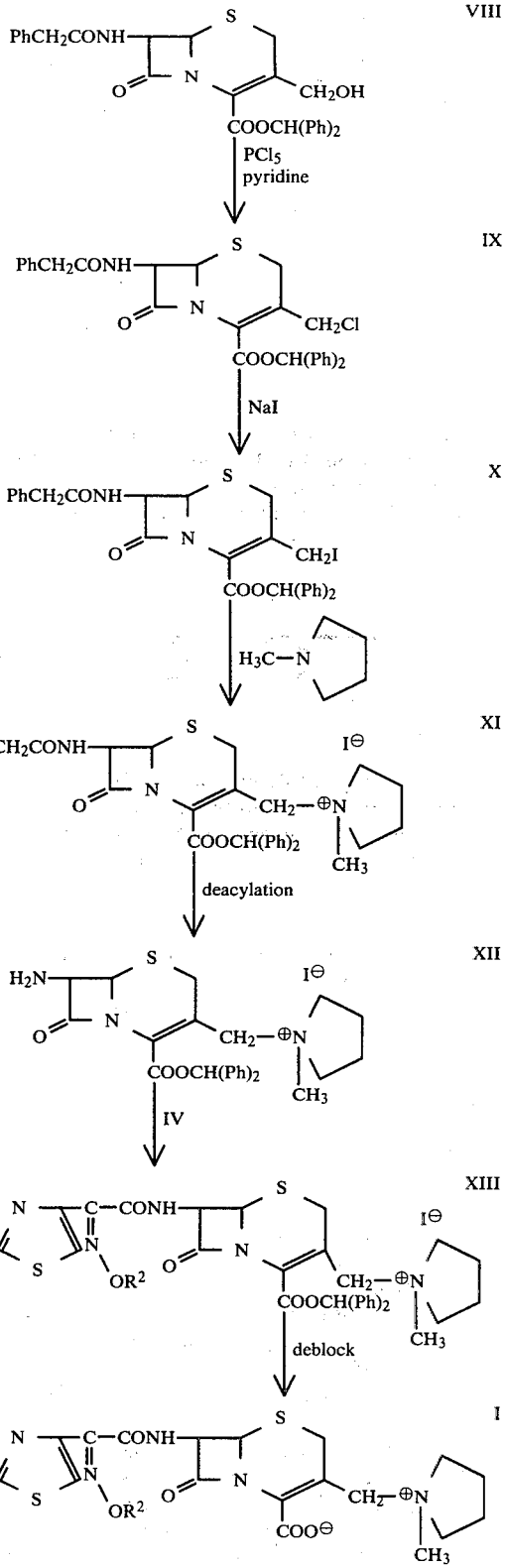

Although the above Reaction Schemes show preferred multi-step procedures for the preparation of the compounds of Formula I, it will be appreciated that other starting materials and procedures may be utilized to prepare the intermediates used in the key step of each Reaction Scheme. Thus, the key step in Reaction Scheme 1 is the reaction of Compound VII with N-methylpyrrolidine. Compound VII may itself be prepared by other procedures. Similarly, the key step in Reaction Scheme 2 is the acylation of Compound XII with Compound IV. Both compounds XII and IV may be prepared by other procedures.

The present invention provides a process for the preparation of compounds of the formula

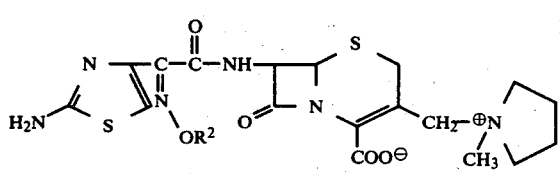

wherein $R^2$ is a straight or branched chain alkyl group containing from 1 to 4 carbon atoms, allyl, 2-butenyl or 3-butenyl, and nontoxic pharmaceutically acceptable salts and solvates thereof, which process comprises reacting a compound of the formula

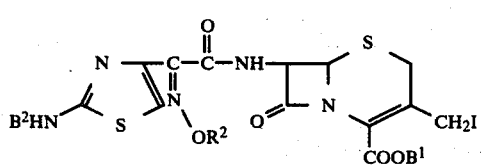

in which $R^2$ is as defined above, $B^1$ is a conventional carboxyl-protecting group and $B^2$ is a conventional amino-protecting group, with N-methylpyrrolidine to produce a compound of the formula

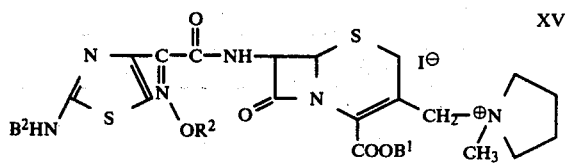

and subsequently removing all protecting groups by conventional means.

The reaction is carried out in a non-aqueous organic solvent such as methylene chloride, chloroform, ethyl ether, hexane ethyl acetate, tetrahydrofuran, acetonitrile and the like, or mixtures of such solvents. The reaction is conveniently carried out at a temperature of from about $-10°$ C. to about $+50°$ C.; we normally prefer to conduct the reaction at room temperature. At least one mole of N-methylpyrrolidine should be used per mole of Compound XIV; we normally prefer to utilize from about 50% to 100% excess of N-methylpyrrolidine.

Carboxyl-protecting groups suitable for use as $B^1$ in the above reaction are well-known to those skilled in the art and include aralkyl groups such as benzyl, p-methoxybenzyl, p-nitrobenzyl and diphenylmethyl (benzhydryl); alkyl groups such as t-butyl; haloalkyl groups such as 2,2,2-trichloroethyl, and other carboxyl-protecting groups described in the literature, e.g. in U.K. Pat. No. 1,399,086. We prefer to utilize carboxyl-protecting groups which are readily removed by treatment with acid. Particularly preferred carboxyl-protecting groups are the benzhydryl and t-butyl moieties.

Amino-protecting groups suitable for use as $B^2$ are also well-known in the art, and include the trityl group and acyl groups such as chloroacetyl. Amino-protecting groups which are readily removed by treatment with acid, e.g. the trityl group, are preferred.

The present invention also provides a process for the preparation of compounds of the formula

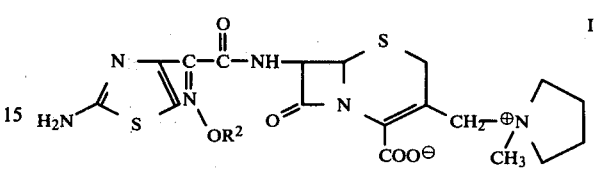

wherein $R^2$ is a straight or branched chain alkyl group containing from 1 to 4 carbon atoms, allyl, 2-butenyl or 3-butenyl, and nontoxic pharmaceutically acceptable salts and solvates thereof, which process comprises acylating a compound of the formula

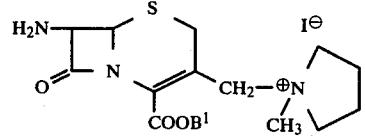

or an N-silyl derivative thereof, in which $B^1$ is hydrogen or a conventional carboxyl-protecting group, with an acylating derivative of an acid of the formula

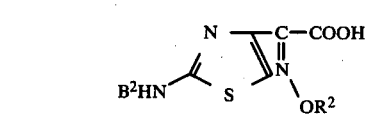

wherein $B^2$ is a conventional amino-protecting group and $R^2$ is as defined above, to produce a compound of the formula

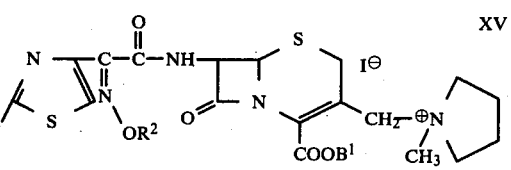

and subsequently removing all protecting groups.

The acylating derivatives of the acid of Formula XVII include the acid halides (and particularly the acid chloride), mixed acid anhydrides (such as the acid anhydrides formed with pivalic acid or a haloformate such as ethyl chloroformate), and activated esters (such as may be formed with N-hydroxybenztriazole in the presence of a condensing agent such as dicyclohexylcarbodiimide). The acylation may also be effected by use of the free acid of Formula XVII in the presence of a condensing agent such as dicyclohexylcarbodiimide, carbonyldiimidazole or an isoxazolium salt. As used herein, the term "acylating derivative" of the acid of Formula XVII includes the free acid itself in the presence of a condensing agent such as described above. The preferred acylating derivative of the acid of Formula XVII is the acid chloride, preferably used in the presence of an acid binding agent (and particularly a tertiary amine acid binding agent such as triethylamine, dimethylaniline or pyridine).

When the acylation is conducted with an acid halide it is possible to utilize an aqueous reaction medium, but a non-aqueous medium is preferred. When acid anhydrides, activated esters, or the free acid in the presence of a condensing agent, are used for the acylation, the reaction medium should be non-aqueous. Particularly preferred solvents for the acylation reaction are halogenated hydrocarbons such as methylene chloride and chloroform, but tertiary amides such as dimethylacetamide or dimethylformamide may be utilized, as well as other conventional solvents such as tetrahydrofuran, acetonitrile and the like.

The acylation reaction may be conducted at a temperature of from about $-50°$ C. to about $+50°$ C. However, it is preferably conducted at or below room temperature and most preferably from about $-30°$ C. to about $0°$ C. It is usually preferred to acylate the compound of Formula XVI with about a stoichiometric amount of the acylating agent of Formula XVII, although a small excess (e.g. 5–25%) of the acylating agent may be utilized.

It is preferable that the compound of Formula XVI be acylated in the form of its N-silyl derivative (when utilizing a non-aqueous reaction medium). This is conveniently done in situ by simply adding a suitable silylating agent (e.g. N,O-bistrimethylsilylacetamide) to the solution of Compound XVI prior to the addition of the acylating agent of Formula XVII. We prefer to utilize about 3 moles of silylating agent per mole of Compound XVI although this is not critical. The silyl compound is readily removed after acylation by the addition of water.

PREPARATION NO. 1

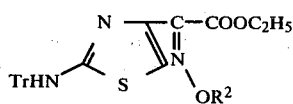

III

Ethyl (Z)-2-Methoxyimino-2-(2-tritylaminothiazol-4-yl)acetate (IIIa)

A mixture of ethyl (Z)-2-hydroxyimino-2-(2-tritylaminothiazol-4-yl) acetate (II) (5.00 g, 10.9 mmoles), $CH_3I$ (2.04 mL, 32.8 mmoles) and $K_2CO_3$ (4.54 g, 32.8 mmoles) in dry dimethylsulfoxide (DMSO) (100 mL) was stirred at room temperature overnight and then poured into water (250 mL). The precipitate which formed was collected by filtration, washed with water and dried to give the title compound (5.15 g, quantitative yield). Mp. $115°$ C. (dec.)

NMR: $\delta^{CDCl_3}$ ppm 1.32 (3H, t), 3.98 (3H, s), 4.30 (2H, q), 6.42 (1H, s), 7.2 (1H, m), 7.25 (15H, s).

Compounds IIIb, IIIc and IIId were prepared by the general procedure set forth above, but replacing the methyl iodide with the appropriate iodide.

| Compound | R² | Yield (%) | Mp (°C.) | Literature[1] Mp (°C.) |
|---|---|---|---|---|
| IIIa | methyl | 100 | 115° (dec.) | ca. 120° (dec.) |
| IIIb | ethyl | 67 | 97–98° | * |
| IIIc | isopropyl | 26 | 52–55° | * |
| IIId | allyl | * | * | * |

*The ester was hydrolyzed without isolation
[1]Tetrahedron, 34, 2233 (1978)

PRPARATION NO. 2

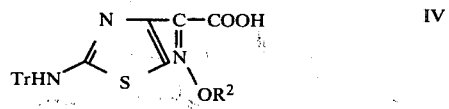

IV

(Z)-2-Methoxyimino-2-(2-tritylaminothiazol-4-yl)acetic acid (IVa)

The ethyl ester IIIa prepared in Preparation No. 1 (6.00 g, 12.7 mmoles) in ethanol (120 mL) was treated with 2 N NaOH (12.7 mL) at room temperature overnight. The reaction mixture was adjusted to pH 8 by the addition of powdered dry ice and the solvent was evaporated under reduced pressure. The residue was dissolved in water (100 mL) and the solution was acidified with 1 N HCl to pH 2 and then extracted with ethyl acetate (3×50 mL). The combined extracts were washed with a saturated aqueous NaCl solution, dried and evaporated. The residue was crystallized from ethyl acetate-hexane to afford 5.56 g (yield 98%) of the title product. Mp. $138°–143°$ C. (dec.).

NMR: $\delta^{CDCl_3}$ ppm 3.89 (3H, s), 6.52 (1H, s), 7.2 (15H, s).

Compounds IVb, IVc and IVd were prepared by the general procedure set forth above.

| Compound | R² | Yield (%) | Mp (°C. dec.) | Literature[1] Mp (°C. dec.) |
|---|---|---|---|---|
| IVa | methyl | 98 | 138–143 | ca. 140 |
| IVb | ethyl | 85 | 140–145 | not reported |
| IVc | isopropyl | 85 | 166–169 | ca. 170 |
| IVd | allyl | 66 | 170–178 | ca. 170 |

[1]Tetrahedron, 34, 2233 (1978)

PREPARATION NO. 3

Benzhydryl 3-Hydroxymethyl-7-phenylacetamido-3-cephem-4-carboxylate (VIII)

To a stirred suspension of phosphate buffer (pH 7, 162.5 mL) and wheat bran (20 g, dry) at room temperature was added 7-phenylacetamidocephalosporanic acid sodium salt (5 gm, 12.1 mmoles) in one portion. The progress of the reaction was monitored by HPLC until the hydrolysis was complete (5 hours). The suspension was filtered to remove the wheat bran and the filtrate was cooled to $5°–10°$ C. for extractive esterification. To the cooled solution was added methylene chloride (32 mL) followed by a 0.5 M solution of diphenyldiazomethane in methylene chloride (24 mL). The pH was then adjusted to 3.0 with 28% phosphoric acid. After 1 hour the reaction mixture was allowed to rise to $20°$ C. Heptane (56 mL) was slowly added and the resulting crystalline title product was recovered by filtration. Yield of the title product was 3.0 gm (50%).

PREPARATION NO. 4

Benzhydryl 7-Amino-3-chloromethyl-3-cephem-4-carboxylate (V)

To a slurry of PCl$_5$ (8.3 g, 40 mmoles) in CH$_2$Cl$_2$ (100 mL) was added pyridine (3.2 g, 40 mmoles) and the mixture was stirred for 20 minutes at 20° C. To the mixture was added benzhydryl 3-hydroxymethyl-7-phenylacetamido-3-cephem-4-carboxylate prepared in Preparation No. 3 (5.1 g, 10 mmoles) with stirring at −40° C., in one portion. The mixture was stirred at −10° C. for 15 minutes and allowed to stand at −10° C. to −15° C. for 7 hours. To the cooled solution (−20° C.) was added propane-1,3-diol (10 mL) and the mixture was allowed to stand at −20° C. for 16 hours and then at room temperature for 20 minutes with stirring. The resulting solution was washed with ice-water (2×20 mL) and saturated aqueous NaCl (10 mL), dried over MgSO$_4$ and concentrated in vacuo. The gummy residue (12 g) was dissolved in a mixture of CHCl$_3$ and n-hexane (2:1), and subjected to chromatography using a silica gel column (200 g) and the same solvent as eluant. Fractions containing the title compound were evaporated in vacuo and the residue triturated with n-hexane to give the title product (2.1 g, 51%), melting at >110° C. (dec.).

IR: $\nu_{KBr}$ 3400, 2800, 1785, 1725 cm$^{-1}$.

UV: $\lambda_{max}^{EtOH}$ 265 nm (E$_1$ $_{cm}$ 1% 160).

NMR: $\delta_{ppm}^{DMSO-d6+CDCl_3}$ 3.69 (2H, s), 4.43 (2H, s), 5.09 (1H, d, J=4.5 Hz), 5.24 (1H, d, J=4.5 Hz), 6.87 (1H, s), 7.3 (10H, m).

EXAMPLE 1

7-[(Z)-2-Methoxyimino-2-(2-aminothiazol-4-yl)acetamido]-3-[(1-methyl-1-pyrrolidinium)methyl]-3-cephem-4-carboxylate (Ia)

A. Benzhydryl 3-Chloromethyl-7-[(Z)-2-methoxyimino-2-(2-tritylaminothiazol-4-yl)acetamido]-3-cephem-4-carboxylate (VIa)

Benzhydryl 7-amino-3-chloromethyl-3-cephem-4-carboxylate prepared in Preparation No. 4 (2.29 g, 5.52 mmoles) in CH$_3$CN (57 mL) was treated with bis(trimethylsilyl)acetamide (BSA, 4.09 mL, 16.6 mmoles) at room temperature for 50 minutes to give a clear solution. To the solution was added an acid chloride solution, which was prepared from (Z)-2-methoxyimino-2-(2-tritylaminothiazol-4-yl)acetic acid (IVa) (2.04 g, 4.60 mmoles) and PCl$_5$ (1.15 g, 5.52 mmoles) in methylene chloride (20 mL). The mixture was stirred at room temperature for 30 minutes, poured into cold water (200 mL) and extracted with ethyl acetate (3×100 mL). The combined extracts were washed with aqueous NaCl, dried and evaporated. The residual syrup (4 g) was chromatographed on a silica gel (150 g) column by eluting with 10:1 and 3:1 mixtures of toluene and ethyl acetate successively. The fractions containing the desired compound were combined and evaporated to afford 2.61 g (68%) of VIa as an amorphous powder.

NMR: $\delta^{CDCl_3}$ ppm 3.50 (2H, s), 4.02 (3H, s), 4.33 (2H, s), 4.98 (1H, d), 5.87 (1H, q), 6.65 (1H, s), 6.90 (1H, s), 7.3 (25H, m).

B. Benzhydryl 3-Iodomethyl-7-[(Z)-2-methoxyimino-2-(2-tritylaminothiazol-4-yl)acetamido]-3-cephem-4-carboxylate (VIIa)

A mixture of the 3-chloromethyl derivative (VIa) (1.50 g, 1.79 mmoles) and NaI (1.34 g, 8.93 mmoles) in methyl ethyl ketone (30 mL) was stirred at room temperature for 1 hour. After evaporation of the solvent the residue was dissolved in ethyl acetate (100 mL) and washed with water, aqueous Na$_2$S$_2$O$_3$ and aqueous NaCl, dried and evaporated to give the title compound VIIa (1.47 g, 89%) as an amorphous powder.

NMR: $\delta^{CDCl_3}$ ppm 3.55 (2H, ABq), 4.00 (3H, s), 4.25 (2H, s), 4.97 (1H, d), 5.80 (1H, q), 6.65 (1H, s), 6.90 (1H, s), 7.3 (25H, m).

C. 7-[(Z)-2-Methoxyimino-2-(2-aminothiazol-4-yl)acetamido]-3-[(1-methyl-1-pyrrolidinium)methyl]-3-cephem-4-carboxylate (Ia)

A mixture of VIIa (4.5 g, 4.83 mmoles) and N-methylpyrrolidine (0.65 mL, 6.28 mmoles) in CH$_2$Cl$_2$ (45 mL) was stirred at room temperature for 20 minutes. Ether (300 mL) was added to the mixture to separate the quaternary salt of the blocked cephalosporin, which was collected by filtration and treated with 90% trifluoroacetic acid (TFA) (40 mL) at room temperature for 1 hour. The mixture was then evaporated under reduced pressure below 20° C. The residue was triturated with ether to give the TFA salt of Ia (2.40 g), which was dissolved in methanol (5 mL) and treated with 1 M solution of sodium-2-ethylhexoate (SEH) in ethyl acetate (8 mL) at room temperature for 30 minutes. After the addition of ethyl acetate (100 mL), the precipitate (1.94 g) formed was collected by filtration. HPLC analysis showed that the crude product was 7% pure with a 1:8 ratio of the Δ$^3$ isomer to the Δ$^2$ isomer. Purification of the product by HPLC was repeated three times (Lichrosorb RP-18, 8×300 mm, eluted with 5% aqueous CH$_3$OH or 0.01 M ammonium phosphate buffer (pH 7.2) containing 5% CH$_3$OH to give 35 mg (1.5%) of the title product as a colorless powder. Estimated purity (by HPLC) 90%. Mp. 150° C. (dec.).

IR: $\nu_{max}^{KBr}$ cm$^{-1}$ 1770, 1660, 1620.

UV: $\lambda_{max}^{phosphate\ buffer,\ pH\ 7}$ nm($\epsilon$) 235 (16200), 258 (15400).

NMR: $\delta^{D_2O}$ ppm 2.31 (4H, m), 3.08 (3H, s), 3.63 (4H, m), 4.09 (3H, s), 5.43 (1H, d, J=4.8 Hz), 5.93 (1H, d), 7.08 (1H, s).

EXAMPLE 2

7-[(Z)-2-Methoxyimino-2-(2-aminothiazol-4-yl)acetamido]-3-[(1-methyl-1-pyrrolidinium)methyl]-3-cephem-4-carboxylate (Ia)

To a stirred solution of 20.4 g (21.9 mmoles) of VIIa in 150 mL of dry methylene chloride was added 2.42 g (28.5 mmoles) of 1-methylpyrrolidine in one portion at room temperature. The mixture was stirred for 5 minutes and poured into 1000 mL of ether with vigorous stirring to form a precipitate, which was filtered, washed with ether (5×30 mL) and dried in vacuo to give 19.3 g of the blocked product as a pale yellow powder.

IR: $\nu_{max}^{KBr}$ cm$^{-1}$ 3400, 1780 (s), 1740, 1675, 1530.

TLC: solvent ethanol-CHCl$_3$ (1:3), Rf=0.30 (Rf=0.95 for VIIa).

The solid was dissolved in 185 mL of trifluoroacetic acid-water (99:1), stirred for 1 hour at room temperature and concentrated to ca. 30 mL below 10° C. The concentrate was poured into 1000 mL of ether with vigorous stirring to form a precipitate, which was filtered, washed with ether (5×40 mL) and dried under vacuum to yield 10.6 g of pale yellow powder. The powder was dissolved in 20 mL of methanol and the solution was filtered. To the filtrate was added 45 mL of 0.8 M SEH in ethyl acetate. The resultant suspension was poured to 400 mL of ethyl acetate and filtered to give 8.08 g of a solid which was a mixture of the title compound and the corresponding $\Delta^2$ isomer ($\Delta^3/\Delta^2 = 1:8$) as shown by HPLC analysis (Lichrosorb RP-18, 10–15% methanol in 0.01 M phosphate buffer, pH 7). A second run from 28.9 g (31.0 mmoles) of VIIa gave 16.0 g of the crude product ($\Delta^3/\Delta^2 = 1:8$). Isolation of the desired $\Delta^3$ isomer from the combined crude product (24.08 g) by using preparative HPLC (System 500, Waters Associates, PrepPAK 500/C$_{18}$, 5–10% CH$_3$OH) afforded 769 mg of Compound Ia.

EXAMPLE 3

7-[(Z)-2-Methoxyimino-2-(2-aminothiazol-4-yl)acetamido]-3-[(1-methyl-1-pyrrolidinium)methyl]-3-cephem-4-carboxylate (Ia)

A series of experiments were conducted to determine the effect of solvent, amount of solvent and reaction time on the yield of Compound Ia and the $\Delta^3/\Delta^2$ ratio in the reaction product. The general procedure was as follows.

To a suspension of the 3-iodomethyl derivative VIIa (45 mg, 0.048 mmole) in the indicated amount of the indicated solvent was added a solution of N-methylpyrrolidine (0.01 mL, 0.097 mmole) in ether (0.1 mL) and the mixture was stirred at room temperature for the indicated period. The reaction mixture was diluted with ether (5 mL) and the resulting precipitate was collected by filtration and mixed with 90% TFA. The mixture was stirred for one hour and evaporated to dryness under reduced pressure below 20° C. to give the product. The ratio of $\Delta^3/\Delta^2$ in the product was determined by HPLC (Lichrosorb RP-18; mobile phase, 0.01 M ammonium phosphate buffer (pH 7.2) containing 15% CH$_3$OH; retention time, $\Delta^3$ 6.60 minutes, $\Delta^2$ 5.56 minutes). Yield of the product and the ratio of $\Delta^3/\Delta^2$ isomers for each experiment are given below.

| Experiment No. | Solvent | Ratio of VIIa (in gms) to Solvent (in mL) | Reaction Time (Min.) | Yield (%) | Ratio $\Delta^3/\Delta^2$ |
| --- | --- | --- | --- | --- | --- |
| 1 | CH$_2$Cl$_2$ | 1:20 | 15 | 73 | 1/8 |
| 2 | CH$_2$Cl$_2$–Ether (1/10) | 1:100 | 15 | 25 | 4/1 |
| 3 | Ethyl acetate-Ether (1/10) | 1:100 | 15 | 27 | 4/1 |
| 4 | Ethyl acetate-Ether (1/10) | 1:100 | 60 | 64 | 2/1 |
| 5 | Ether | 1:100 | 15 | 31 | 6/1 |
| 6 | Ether | 1:100 | 60 | 62 | 3/1 |
| 7 | Ether | 1:60 | 15 | 55 | 3.5/1 |
| 8 | Ether | 1:60 | 60 | 82 | 1/1 |

EXAMPLE 4

7-[(Z)-2-Ethoxyimino-2-(2-aminothiazol-4-yl)acetamido]-3-[(1-methyl-1-pyrrolidinium)methyl]-3-cephem-4-carboxylate (Ib)

A. Benzhydryl 3-Chloromethyl-7-[(Z)-2-ethoxyimino--(2-tritylaminothiazol-4-yl)acetamido]-3-cephem-4-carboxylate (VIb)

To a solution of (Z)-2-ethoxyimino-2-(2-tritylaminothiazol-4-yl)acetic acid (IVb) (1.095 g, 2.4 mmoles) in dichloromethane (20 mL) was added phosphorus pentachloride (500 mg). After stirring for 1 hour at room temperature, the mixture was added in one portion to an ice-cooled solution of Compound V (1.083 g, 2.4 mmoles) and BSA (1 mL) in dichloromethane (20 mL). After stirring for 0.5 hour the reaction mixture was poured into 10% aqueous NaHCO$_3$ (200 mL) and extracted with CHCl$_3$ (100 mL). The extract was washed with water, dried over MgSO$_4$, and evaporated under reduced pressure. The residue was chromatographed on a silica gel column. Elution with CHCl$_3$ gave VIb as an amorphous powder, 1.76 g (86%).

NMR: $\delta^{CDCl_3}$ ppm 1.40 (3H, t, CH$_2$CH$_3$), 3.53 (2H, ABq, 2-CH$_2$), 4.37 (2H, s, —CH$_2$Cl), 4.60 (2H, q, —CH$_2$CH$_3$), 4.90 (1H, d, 6-H), 5.89 (1H, d, 7-H), 6.88 (1H, s, thiazole-H), 6.91 (1H, s, benzhydryl-CH).

B. Diphenylmethyl 7-[(Z)-2-Ethoxyimino-2-(2-tritylaminothiazol-4-yl)acetamido]-3-iodomethyl-3-cephem-4-carboxylate (VIIb)

A mixture of VIb (1.07 g, 1.25 mmoles) and NaI (562 mg, 2.75 mmoles) in acetone (20 mL) was stirred for 1 hour. The mixture was filtered and the filtrate was poured into water and extracted with ethyl acetate. The organic layer was washed successively with 5% aqueous Na$_2$S$_2$O$_3$, water and saturated aqueous NaCl, dried over MgSO$_4$ and evaporated to give 1.04 g (89%) of Compound VIIb.

NMR: $\delta^{CDCl_3}$ ppm 3.55 (2H, q, 2-CH$_2$), 4.27 (2H, s, CH$_2$I), 5.02 (1H, d, 6-H), 5.87 (1H, d, 7-H), 6.68 (1H, s, thiazole ring H), 6.93 (1H, s, benzhydryl-CH).

C. 7-[(Z)-2-Ethoxyimino-2-(2-aminothiazol-4-yl)acetamido]-3-[(1-methyl-1-pyrrolidinium)methyl]-3-cephem-4-carboxylate (Ib)

A mixture of VIIb (333 mg, 0.35 mmole) and N-methylpyrrolidine (60 mg, 0.7 mmole) in CH$_2$Cl$_2$ (5 mL) was stirred for 0.5 hour at room temperature and then evaporated in vacuo. The residue was washed with ether and dissolved in 90% aqueous TFA. After standing for 0.5 hour at room temperature the mixture was concentrated under reduced pressure. Ether was added to the concentrate to separate the quaternized product, which was collected by filtration and dissolved in a small amonunt of methanol. The solution was chromatographed on an HP-20 column (40 mL). Elution with 30% aqueous CH$_3$OH followed by lyophilization afforded 0.062 g of a mixture of the $\Delta^2$ and $\Delta^3$ isomer ($\Delta^2:\Delta^3 = 5:1$). The mixture was purified by HPLC (Lichrosorb RP-18, 8×300 mm, 15% methanol) and the desired $\Delta^3$ isomer (Ib) was isolated as pale yellow powder, 4.9 mg (2.7%).

UV: $\lambda_{max}^{phosphate\ buffer,\ pH\ 7}$ nm($\epsilon$) 235 (15000), 258 (14000).

NMR: $\delta^{D_2O}$ ppm 1.43 (3H, t), 2.33 (4H, m), 3.10 (3H, s), 3.64 (4H, m), 4.36 (2H, q), 5.44 (1H, d), 5.95 (1H, d), 7.08 (1H, s).

EXAMPLE 5

7-[(Z)-2-(2-Propoxyimino)-2-(2-aminothiazol-4-yl)acetamido]-3-[(1-methyl-1-pyrrolidinium)methyl]-3-cephem-4-carboxylate (Ic)

A. Diphenylmethyl 3-Chloromethyl-7-[(Z)-2-(2-propoxyimino)-2-(2-tritylaminothiazol-4-yl)acetamido]-3-cephem-4-carboxylate (VIc)

A mixture of (Z)-2-(2-propoxyimino)-2-(2-tritylaminothiazol-4-yl)acetic acid (IVc) (707 mg, 1.5 mmoles) and phosphorus pentachloride (344 mg, 1.65 mmoles) in dichloromethane (14 mL) was stirred at room temperature for 1 hour and poured into a solution of Compound V (677 mg, 1.5 mmoles) and BSA (1.1 mL, 4.5 mmoles) in dichloromethane (15 mL). The reaction mixture was stirred at room temperature for 30 minutes, diluted with ethyl acetate (200 mL), washed with aqueous sodium bicarbonate (100 mL) and water (3×100 mL), dried over sodium sulfate and evaporated to give 1.4 g (100%) of Compound VIc.

IR: $\nu_{max}^{KBr}$ cm$^{-1}$ 3360, 3020, 3060, 2960, 1785, 1725, 1680, 1520, 1500, 1450, 1375, 1300, 1250, 1160, 1090, 1060, 1010, 990, 900, 840, 750, 700.

UV: $\lambda_{max}^{EtOH}$ nm($\epsilon$) 240 (24600), 260 (20700).

NMR: $\epsilon^{CDCl_3}$ ppm 1.35 (6H, d, J=6 Hz), 3.50 (2H, s), 4.35 (2H, s), 4.58 (1H, m, J=6 Hz), 5.00 (1H, d, J=4.5 Hz), 5.91 (1H, d-d, J=4.5 and 9 Hz; d by D$_2$O, J=4.5 Hz), 6.68 (1H, s), 6.88 (1H, s), 7.25 (25H, s).

B. Diphenylmethyl 3-Iodomethyl-7-[(Z)-2-(2-propoxyimino)-2-(2-tritylaminothiazol-4-yl)acetamido]-3-cephem-4-carboxylate (VIIc)

A mixture of Compound VIc (500 mg, 0.55 mmole) and sodium iodide (248 mg, 1.66 mmoles) in acetone (10 mL) was stirred at room temperature for 50 minutes. After evaporation, the residue was dissolved in ethyl acetate (15 mL), washed successively with 10% aqueous sodium thiosulfate (10 mL), water (10 mL) and aqueous NaCl (10 mL), dried over sodium sulfate and evaporated to yield 494 mg (90%) of the title compound (VIIc).

IR: $\nu_{max}^{KBr}$ cm$^{-1}$ 3360, 3040, 3020, 2960, 1785, 1720, 1680, 1600, 1520, 1500, 1450, 1370, 1300, 1230, 1150, 1115, 1080, 990, 900, 840, 750, 700.

UV: $\lambda_{max}^{EtOH}$ nm($\epsilon$) 240 (24900), 260 (19400).

NMR: $\delta^{CDCl_3}$ ppm 1.30 (6H, d, J=6 Hz), 3.37 and 3.70 (1H each, d, J=16 Hz), 4.22 (2H, s), 4.55 (1H, m, J=6 Hz), 4.95 (1H, d, J=4.5 Hz), 5.83 (1H, d-d, J=4.5 and 9 Hz; d by D$_2$O), 6.66 (1H, s), 6.87 (1H, s), 7.25 (25H, s).

C. 7-[(Z)-2-(2-Propoxyimino)-2-(2-aminothiazol-4-yl)acetamido]-3-[(1-methyl-1-pyrrolidinium)methyl]-3-cephem-4-carboxylate (Ic)

A mixture of the Compound VIIc (545 mg, 0.55 mmole) and 1-methylpyrrolidine (70 mg, 0.82 mmole) in dichloromethane (10 mL) was stirred at room temperature for 30 minutes and diluted with ether (100 mL). The resulting precipitate was collected by filtration. A solution of the precipitate in 90% TFA (4.5 mL) was stirred at room temperature for 30 minutes and evaporated in vacuo. The residue was triturated with ether to give 317 mg of the crude product, which was chromatographed on an HP-20 column (50 mL), eluted with water (500 mL) and 30% CH$_3$OH (500 mL). The 30% CH$_3$OH eluate was concentrated and lyophilized to yield 109 mg of a mixture of the $\Delta^2$ and $\Delta^3$ isomers ($\Delta^2/\Delta^3$=6/1), 100 mg of which was purified by HPLC (Lichrosorb RP-18, 15% MeOH) to give 5 mg (3%) of the desired title Compound Ic.

UV: $\lambda_{max}^{pH\ 7\ buffer}$ nm($\epsilon$) 236 (15100), 252 (14600).

NMR: $\delta^{D_2O}$ ppm 1.42 (6H, d, J=6 Hz), 2.33 (4H, s), 3.10 (3H, s), 3.65 (4H, s), 3.83 and 4.23 (1H each, d, J=17 Hz), 5.45 (1H, d, J=4.5 Hz), 5.95 (1H, d, J=4.5 Hz), 7.05 (1H, s).

EXAMPLE 6

7-[(Z)-2-Allyloxyimino-2-(2-aminothiazol-4-yl)acetamido]-3-[(1-methyl-1-pyrrolidinium)methyl]-3-cephem-4-carboxylate (Id)

A. Benzhydryl 7-[(Z)-2-Allyloxyimino-2-(2-tritylaminothiazol-4-yl)acetamido]-3-chloromethyl-3-cephem-4-carboxylate (VId)

To a suspension of Compound V (1.35 g, 3 mmoles) in methylene chloride (20 mL) was added BSA (1.1 mL, 4.5 mmoles), and the mixture was stirred for 30 minutes at room temperature to become a clear solution. A mixture of (Z)-2-allyloxyimino-2-(2-tritylaminothiazol-4-yl)acetic acid (IVd) (1.40 g, 3.0 mmoles) and phosphorus pentachloride (690 mg, 3.3 mmoles) in methylene chloride (20 mL) was stirred for 15 minutes at room temperature and poured in one portion into the solution of the trimethylsilylated Compound V. The mixture was stirred for 20 minutes at room temperature and diluted with ethyl acetate (200 mL), washed with aqueous sodium bicarbonate and water, dried and evaporated under reduced pressure. The oily residue was purified by silica gel column chromatography (Wakogel, C-200, 30 g). The column was eluted with chloroform and the fractions containing the desired product were combined. Evaporation under reduced pressure afforded the title compound (VId) as an amorphous powder, yield 2.32 g (89%). Mp. 100–115° C. (dec.).

IR: $\nu_{max}^{KBr}$ cm$^{-1}$ 3390, 1790, 1730, 1680, 1530, 1380, 1250, 1160, 1020.

NMR: $\delta^{CDCl_3}$ ppm 3.50 (2H, 2-H), 4.32 (2H, s, 3-CH), 4.6–6.1 (7H, m, CH$_2$CH=CH$_2$ and 6,7-H), 6.70 (1H, s, thiazole-H), 6.90 (1H, s, Ph$_2$CH), 7.1–7.6 (30H, m, phenyl protons).

Anal. Calc'd. for C$_{48}$H$_{40}$N$_5$O$_5$S$_2$Cl·$\frac{1}{2}$CHCl$_3$: C, 64.05; H, 4.45; N, 7.73; S, 7.08; Cl, 7.82. Found: C, 64.13, 63.99; H, 4.61, 4.64; N, 7.50, 7.30; S, 6.85, 6.85; Cl, 7.55, 7.46.

B. Benzhydryl 7[(Z)-2-Allyloxyimino-2-(tritylaminothiazol)-4-yl)acetamido]-3-iodomethyl-3-cephem-4-carboxylate (VIId)

A mixture of Compound VId (2.30 g, 2.65 mmoles) and sodium iodide (2 g, 13.3 mmoles) in acetone (15 mL) was stirred for 1 hour at room temperature and then evaporated under reduced pressure. A solution of the oily residue in ethyl acetate (200 mL) was washed with 10% sodium thiosulfate and water, evaporated under reduced pressure to afford Compound VIId as an amorphous powder, which was used in the next step without further purification. Yield 2.52 g (99%).

C. 7-[(Z)-2-Allyloxyimino-2-(2-aminothiazol-4-yl)acetamido]-3-[(1-methyl-1-pyrrolidinium)methyl]-3-cephem-4-carboxylate (Id)

A mixture of Compound VIId (478 mg, 0.5 mmole) and N-methylpyrrolidine (0.05 mL, 0.5 mmole) in methylene chloride (5 mL) was stirred for 20 minutes at room temperature and diluted with ether (50 mL) to precipitate the quaternized product (yield 500 mg). A mixture of the quaternized product and TFA (2 mL) was allowed to stand at room temperature for 1.5 hours and diluted with ether to precipitate the crude TFA salt of the product (yield 265 mg), which was chromtographed on a column of HP-20 (1.8×18 cm). The column was eluted with water and 30% aqueous methanol. The methanolic eluate was evaporated under reduced pressure and the residue was freeze-dried to give an amorphous powder (yield 124 mg), which contained the desired product (17%) and the corresponding $\Delta^2$ isomer (83%). The mixture was purified by HPLC (Lichrosorb RP-18; 0.01 M NH$_4$H$_2$PO$_4$ (pH 7):CH$_3$OH==85:15). The eluate was acidified to pH 3 with dilute HCl and chromatographed on a column of HP-20 (1.8×10 cm). The column was eluted with water and then with 30% aqueous methanol. The methanolic eluate was evaporated under reduced pressure and the residue was freeze dried to afford the title compound (Id) as an amorphous powder (yield 13 mg, 5.1%). Mp. 155° C. (dec.).

IR: $\nu_{max}^{KBr}$ cm$^{-1}$ 3600-2800, 1770, 1670, 1610, 1530, 1200.

UV: $\lambda_{max}^{pH\ 7\ buffer}$ nm($\epsilon$) 235 (16600), 253 (15600).

NMR: $\delta^{D2O}$ ppm 2.1–2.5 (4H, m, pyrrolidine-H), 3.10 (3H, s, $^{30}$NCH$_3$), 3.4–3.8 (4H, m, pyrrolidine-H), 5.95 (1H, d, 4 Hz, 7-H), 7.10 (1H, s, thiazole-H).

We claim:

1. A compound of the formula

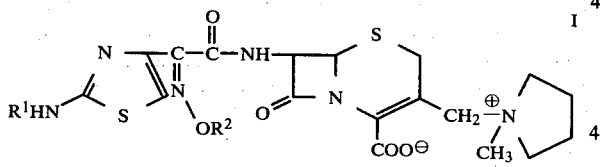

wherein R$^1$ is hydrogen or a conventional amino-protecting group, and R$^2$ is a straight or branched chain alkyl group containing from 1 to 4 carbon atoms, allyl, 2-butenyl or 3-butenyl, or a nontoxic pharmaceutically acceptable salt or solvate thereof.

2. The compound of claim 1 which is 7-[(Z)-2-methoxyimino-2-(2-aminothiazol-4-yl)acetamido]-3-[(1-methyl-1-pyrrolidinium)-methyl]-3-cephem-4-carboxylate, or a nontoxic pharmaceutically acceptable salt or solvate thereof.

3. The compound of claim 1 which is 7-[(Z)-2-ethoxyimino-2-(2-aminothiazol-4-yl)acetamido]-3-[(1-methyl-1-pyrrolidinium)-methyl]-3-cephem-4-carboxylate, or a nontoxic pharmaceutically acceptable salt or solvate thereof.

4. The compound of claim 1 which is 7-[(Z)-2-(2-propoxyimino)-2-(2-aminothiazol-4-yl)acetamido]-3-[(1-methyl-1-pyrrolidinium)methyl]-3-cephem-4-carboxylate, or a nontoxic pharmaceutically acceptable salt or solvate thereof.

5. The compound of claim 1 which is 7-[(Z)-2-Allyloxyimino-2-(2-aminothiazol-4-yl)acetamido]-3-[(1-methyl-1-pyrrolidinium)methyl]-3-cephem-4-carboxylate, or a nontoxic pharmaceutically acceptable salt or solvate thereof.

6. A method of combatting bacterial infection in a warm-blooded mammal in need of such treatment comprising administering to said warm-blooded mammal an antibacterially effective amount of at least one compound of claim 1.

7. The method of claim 6 wherein the compoound of claim 1 is 7-[(Z)-2-methoxyimino-2-(2-aminothiazol-4-yl)acetamido]-3-[(1-methyl-1-pyrrolidinium)methyl]-3-cephem-4-carboxylate or a nontoxic pharmaceutically acceptable salt or solvate thereof.

8. An antibacterial composition comprising an antibacterially effective amount of at least one compound of claim 1 and an inert pharmaceutical carrier.

9. The composition of claim 8 wherein the compound of claim 1 is 7-[(Z)-2-methoxyimino-2-(2-aminothiazol-4-yl)-acetamido]-3-[(1-methyl-1-pyrrolidinium)methyl]-3-cephem-4-carboxylate or a nontoxic pharmaceutically acceptable salt or solvate thereof.

10. An antibacterial composition in unit dosage form comprising from about 50 mg to about 1500 mg of at least one compound of claim 1 and an inert pharmaceutical carrier.

11. The composition of claim 10 wherein the compound of claim 1 is 7-[(Z)-2-methoxyimino-2-(2-aminothiazol-4-yl)-acetamido]-3-[(1-methyl-1-pyrrolidinium)-methyl]-3-cephem-4-carboxylate or a nontoxic pharmaceutically acceptable salt or solvate thereof.

* * * * *

UNITED STATES PATENT AND TRADEMARK OFFICE
CERTIFICATE OF CORRECTION

PATENT NO. : 4,406,899

DATED : September 27, 1983

INVENTOR(S) : Shimpei Aburaki et al.

It is certified that error appears in the above—identified patent and that said Letters Patent is hereby corrected as shown below:

In Column 4, the numbering ("I") of the structural formula at Line 45 should be deleted.

In Column 4, the structural formula at Line 65 should be numbered -- I -- .

In Column 7, the structural formula at Line 30 should be numbered -- IV -- .

In Column 7, the structural formula at Line 35 should be numbered -- V -- .

Signed and Sealed this

Thirteenth Day of December 1983

[SEAL]

Attest:

GERALD J. MOSSINGHOFF

Attesting Officer

Commissioner of Patents and Trademarks